US009120765B2

(12) United States Patent
Lain et al.

(10) Patent No.: US 9,120,765 B2
(45) Date of Patent: Sep. 1, 2015

(54) P53 ACTIVATING COMPOUNDS

(71) Applicants: University Court of the University of Dundee, Dundee (GB); University Court of the University of St. Andrews, St. Andrews (GB)

(72) Inventors: Sonia Lain, Dundee (GB); David Phillip Lane, St. Andrews (GB); Michael John Raymond Stark, Newport on Tay (GB); Anna Rose McCarthy, Dundee (GB); Jonathan James Hollick, Inchture (GB); Nicholas James Westwood, Dundee (GB)

(73) Assignees: University Court of the University of Dundee, Dundee (GB); University Court of the University of St. Andrews, St. Andrews (GB)

( * ) Notice: Subject to any disclaimer, the term of this patent is extended or adjusted under 35 U.S.C. 154(b) by 0 days.

(21) Appl. No.: 13/886,898

(22) Filed: May 3, 2013

(65) Prior Publication Data

US 2013/0310382 A1    Nov. 21, 2013

Related U.S. Application Data

(62) Division of application No. 12/439,906, filed as application No. PCT/GB2007/003302 on Sep. 4, 2007, now Pat. No. 8,501,991.

(30) Foreign Application Priority Data

Sep. 4, 2006 (GB) .................................... 0617278.7
Dec. 23, 2006 (GB) .................................... 0625929.5

(51) Int. Cl.
| A61K 31/5375 | (2006.01) |
| A61K 31/17 | (2006.01) |
| C07D 295/12 | (2006.01) |
| C07C 335/16 | (2006.01) |
| C07D 295/155 | (2006.01) |
| C07C 275/54 | (2006.01) |
| C07C 335/26 | (2006.01) |
| C07D 295/15 | (2006.01) |

(52) U.S. Cl.
CPC .......... *C07D 295/155* (2013.01); *C07C 275/54* (2013.01); *C07C 335/26* (2013.01); *C07D 295/15* (2013.01)

(58) Field of Classification Search
USPC .................. 514/237.8, 584; 564/23; 544/165
See application file for complete search history.

(56) References Cited

U.S. PATENT DOCUMENTS

2004/0138465 A1   7/2004  Spurr
2006/0004085 A1   1/2006  Weber et al.

FOREIGN PATENT DOCUMENTS

| EP | 0116728 | 8/1984 |
| EP | 0117320 | 9/1984 |
| EP | 0136745 | 4/1985 |
| EP | 0193249 | 9/1986 |
| EP | 0475506 | 3/1992 |
| EP | 0545441 | 6/1993 |
| JP | 07285952 | 10/1995 |
| WO | WO95/25096 | 9/1995 |
| WO | WO2004/014885 | 2/2004 |
| WO | WO2006/083271 | 8/2006 |
| WO | WO2006/110762 | 10/2006 |

OTHER PUBLICATIONS

International Preliminary Report on Patentability (excluding amended sheets) for International Application No. PCT/GB2007/003302, Date of completion of report: Oct. 29, 2008.
International Search Report for International Application No. PCT/GB2007/003302 mailed on Feb. 20, 2008.
Written Opinion of the International Searching Authority for International Application No. PCT/GB2007/003302, 2008.
Berkson et al., Pilot screening programme for small molecule activators of p53, Int. J. Cancer: 115, 701-710 (2005).
Heltweg et al., Antitumor Activity of a Small-Molecule Inhibitor of Human Silent Information Regulator 2 Enzymes, Cancer Res 2006; 66(8): 4368-4377.
Hollick et al., Poster of: High-throughput Screening to Identify Novel Inducers of p53 Function, University of St. Andrews and University of Dundee, Sep. 2004.
Hollick et al., Abstract, High-throughput Screening to Identify Novel Inducers of p53 Function, University of St. Andrews and University of Dundee, Sep. 2004.
Patents Act 1977: Search Report under Section 17 for Application No. GB0617278.7 dated Jan. 19, 2007.
Sohn et al., High-throughput measurement of the Tp53 response to anticancer drugs and random compounds using a stably integrated, Carcinogenesis, vol. 23, No. 6, pp. 949-957, 2002.
STN Chemcats database, Accession No. 2004:2163350 & ChemStar Product List Apr. 6, 2006.
STN Chemcats database, Accession No. 2004:2163352 & ChemStar Product List Apr. 6, 2006.
STN Chemcats database, Accession No. 2004:2167954 & ChemStar Product List Apr. 6, 2006.
STN Chemcats database, Accession No. 2005:4236088 & Scientific Exchange Product List Mar. 14, 2006.
STN Chemcats database, Accession No. 2005:4563741 & Scientific Exchange Product List Mar. 14, 2006.
STN Chemcats database, Accession No. 2006:1409306 & Aurora Screening Library May 10, 2006.
Thakar et al., Synthesis of thiourea derivatives bearing the benzo[b]thiophene nucleus as potential antimicrobial agents, J. Serb. Chem. Soc., 2005, pp. 807-815, vol. 70, No. 6.
Vassilev et al., In Vivo Activation of the p53 Pathway by Small-Molecule Antagonists of MDM2, Science, vol. 303, 2004, pp. 844-848.

*Primary Examiner* — Nyeemah A Grazier
(74) *Attorney, Agent, or Firm* — MyersBigel Sibley & Sajovec, P.A.

(57) ABSTRACT

The present invention relates to compounds which activate the p53 response, and find use in, for example, hyperproliferative diseases such as cancer treatment and potentially other diseases/conditions involving sirtuin function.

28 Claims, 5 Drawing Sheets

P53 ACTIVATING COMPOUNDS

CROSS-REFERENCE TO RELATED APPLICATIONS

This application is a divisional application of U.S. application Ser. No. 12/439,906, filed Oct. 12, 2010, allowed, which is a 35 U.S.C. §371 national phase application of International Application No. PCT/GB2007/003302, filed Sep. 4, 2007, which claims the benefit of U.K. Patent Application No. GB 0617278.7, filed Sep. 4, 2006 and U.K. Patent Application No. GB 0625929.5, filed Dec. 23, 2006, the contents of all of which are incorporated by reference herein in their entireties.

INTRODUCTION

The present invention relates to compounds which activate the p53 response, and find use in, for example, hyperproliferative diseases such as cancer treatment and potentially other diseases/conditions (involving sirtuin function).

BACKGROUND

The p53 tumour suppressor protein is a central mediator of cellular stress response. The function of p53 plays a major role in preventing tumour development. It responds to a range of potentially oncogenic stresses by activating protective mechanisms, most notably cell cycle arrest and apoptosis. Its importance as a tumour suppressor is reflected by its high rate of mutation in human cancer, with >50% of adult human tumours bearing inactivating mutations or deletions in the TP53 gene. In many cancers where p53 is wild-type, the p53 pathway may be altered by other oncogenic events. This means that the p53 response is probably defective in most cancers.

Contrary to the findings in solid tumours in adults, the occurrence of p53 mutations in virus-associated malignancies (e.g., cervical cancer), haematological malignant diseases and childhood cancer is very low. This may be the key to the much better prognosis of children with cancer compared to adults. When considering long term therapies or treatment of young patients, however, it is important to be aware of the mutagenic effects of many current therapies. Additionally, literature shows that treatment of B-CLL patients with DNA-damaging alkylating agents correlates with the appearance of mutations in p53 that are associated significantly with poor outcome and drug resistance. Improving the treatment of those cancers in which p53 function is not abolished by mutation may depend on finding novel non-genotoxic activators of the p53 response.

Many current anti-cancer therapies activate the p53 response via DNA damage. Non-genotoxic activation of the p53 pathway may open the way to long-term, including, prophylactic treatments for cancer. Molecules which are consistent with this requirement may be useful as therapeutic agents for the management of patients with hyperproliferative conditions, without abolishing p53 function by mutation.

It is an object of the present invention to provide molecules, and the use of those molecules, for the treatment and/or prophylaxis of conditions and diseases involving abnormal p53 function, such as hyperproliferative conditions, such as cancer, and related conditions.

It is a further object of the present invention to provide molecules, and the use of those molecules, for the treatment and/or prophylaxis of conditions and diseases associated with sirtuin 1(SirT1) expression and/or function, such as cancer, diabetes, muscle differentiation, heart failure, neurodegeneration, aging, HIV infection and malaria.

SUMMARY OF THE INVENTION

According to a first aspect of the present invention there is provided use of a compound according to formula (I) as a medicament:

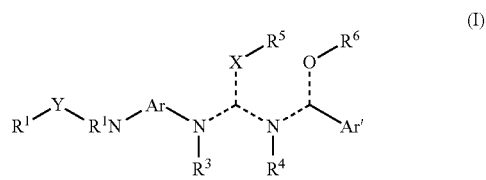

(I)

wherein, $R^1$ is H; branched or unbranched substituted or unsubstituted alkyl, alkenyl or alkynyl; or aryl; or comprises a group which links to a label, probe or solvent solubilising group;

$R^2$ is a $C_2$-$C_{10}$ branched or unbranched, substituted or unubstituted alkyl;

Y is absent or —C(O)— or —SO$_2$—;

Ar is aryl;

X is O or S;

$R^3$ and $R^4$ are independently absent or present and when present are independently H or branched or unbranched, substituted or unsubstituted alkyl or $R^3$ and $R^4$ are bound together to form a branched or unbranched, substituted or unsubstituted alkylene;

$R^5$ and $R^6$ are independently absent or present and when present are independently branched or unbranched, substituted or unsubstituted alkyl; and wherein, when $R^3$ is present, the dashed line b is a single bond, and when $R^3$ is absent, the dashed line b is a double bond;

when $R^4$ is present, the dashed lines c and d are single bonds, and when $R^4$ is absent, one of the dashed lines c or d is a double bond and the other is a single bond; and, when $R^5$ and $R^6$ are absent, the dashed lines a and e respectively are double bonds, and when $R^5$ and $R^6$ are present, the dashed lines a and e respectively are single bonds, or a physiologically acceptable salt, solvate, ester or other physiologically functional derivative thereof.

Thus, the single or double bond requirements of the dashed lines a, b, c, d and e, are chosen to ensure that the tetra-valency of the associated carbon, and tri-valency of the nitrogen atoms, is maintained. It is noted, however, that the nitrogen atoms may become tetra-valent and positively charged though bonding of an H or other moiety e.g. alkyl group, thereto.

Thus, for the avoidance of doubt, variations of the compounds of formula (I) may be represented by the following compound formulae (IA-D):

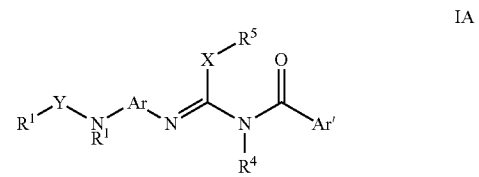

IA

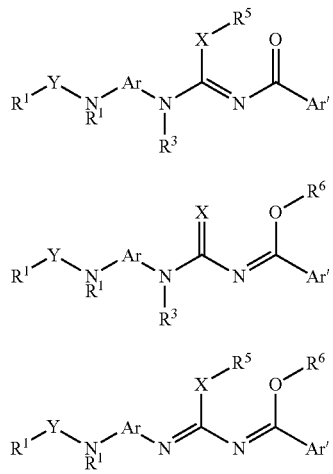

Without wishing to be bound by theory, from studying structure-activity relationships, it appears that the grouping in formula (I) of $R^1$—Y—NH— provides the activity by providing a hydrogen bond donor group, e.g. as provided for by the NH moiety. It also appears that $R^2$ is preferably a sterically bulky group.

Y may be present or absent, but is preferably present. Y is preferably a —C(O)— group.

X is preferably a sulphur atom.

$R^1$ is preferably a substituted or unsubstituted alkyl or aryl group.

Preferably, $R^2$ is a branched alkyl group, such as a secondary or tertiary alkyl group.

Most preferably, $R^2$ is an iso-propyl or tertiary butyl group (i.e. tert-butyl).

It is preferred that the $R^2$ group is positioned in the para-position of the phenyl ring to which it is bonded.

The aryl group, Ar may be a substituted or unsubstituted monocyclic or polycyclic aryl or heteroaryl moiety.

Preferably, Ar is phenyl.

When Ar is phenyl, it is preferred that the groups bonded thereto are in the para-position, i.e. the —NH— is para- to the group —$NR^3$—.

Preferably, $R^5$ and $R^6$ are absent, such that the dashed lines a and e are double bonds.

Preferably, $R^3$ and $R^4$ are present, and preferably are hydrogen or $C_1$-$C_4$ alkyl, e.g. methyl.

References to alkyl, alkenyl and alkynyl herein include references to branched or unbranched substituted or unsubstituted linear or cyclic versions of those groups.

References to aryl herein include references to substituted or unsubstituted monocyclic or polycyclic aryl or heteroaryl.

When $R^1$ is not H, it may be substituted one or more times with a group independently selected, at each occurrence, from the group consisting of alkyl, alkenyl, alkynyl, aryl or heteroaryl, carboxy, alkyloxycarbonyl hydroxyl, amino, morpholino, nitro, alkyloxy, alkylthio, formyl, cyano, carbamoyl, halo (e.g. fluoro, chloro, bromo or iodo), a ketone, —S(O)$NR^7R^8$ or —S(O)$R^9$, wherein $R^7$, $R^8$ and $R^9$ are each independently selected from alkyl, alkenyl, alkynyl, aryl or heteroaryl.

Typically, $R^1$ is an alkyl group, preferably a $C_3$-$C_6$ straight chain alkyl, e.g. a $C_4$ alkyl, e.g. n-butyl.

Typically, the alkyl group is substituted at the free terminal end with a substituent selected from phenyl, hydroxyl, amino, morpholino, nitro, alkyloxy, alkylthio, formyl, cyano, carbamoyl, halo (e.g. fluoro, chloro, bromo or iodo), a ketone, —S(O)$NR^7R^8$ or —S(O)$R^9$, wherein $R^7$, $R^8$ and $R^9$ are each independently selected from alkyl, alkenyl, alkynyl, aryl or heteroaryl.

When the terminal substituent is a morpholino group, it is preferably bonded to the terminous of $R^1$ by its nitrogen atom.

The terminal substituent may be a halogen, e.g. bromo, thus providing an $R^1$ group having the formula $Br(CH_2)_4$—.

When the terminal substituent is an amino or morpholino group, the nitrogen atom thereof may be protonated (e.g. from the action of an acid) to form a positively charged species.

$R^1$ may advantageously be considered as a linker group to link to a label, probe and/or water soluble group. For example, the linker may link the remaining part of the compound according to formula (I) (i.e. the active compound) to a label or probe used in biochemical experiments, for example, to provide molecules having utility in mechanism of action studies. The linker may be any suitable moiety for this purpose, such as an alkyl chain, polymers of ethylene glycol (i.e. $(OCH_2CH_2)_{n1}$) and peptides of 6-aminohexanoic acid (i.e. $(NH(CH_2)_5CO)_{n2}$), wherein n1 and n2 indicate that the molecule is a polymer, and typically are integers ranging from 1 to about 6. Labels and probes include entities known for such purposes, such as, biotin, streptavadin, fluorophores (e.g. bodipy, fluorescein and rhodamine), radioactive labels and solid phase matrices, e.g. polymers such as polymer beads, for example polystyrene. Water solubilising groups include groups suitable for such purpose, including sugars, amines, amino acids, phosphates and the like, and salts of these.

A water solubilising group may be used to modify the solubility of the active compound to alter, e.g. to optimise, the bioavailability and/or pharmacokinetics of the compound, particularly when used as a pharmaceutical.

References to amino herein, include references to cyclic amino groups, i.e. wherein the nitrogen atom of the amine is a member of a ring.

References to amino herein, also include references to protonated versions of the amines, and salts thereof. For example, the amine may be protonated and form a salt with a number of acids, such as hydrochloric acid, sulphuric acid and the like, including carboxylic acids. For example, the hydrochloride salts of an amine may exhibit increased solubility in water and aqueous solvents.

In formula (I), the aryl moiety may be, for example, a 5- or 6-membered monocyclic aryl or heteroaryl ring structure or other polycyclic aryl or heteroaryl moiety.

Phenyl is an example of a 6-membered aryl group.

Typically, the heteroatom in the heteroaryl structure is selected from oxygen or nitrogen.

Furyl and pyrrolyl are examples of 5-membered heteroaryl groups containing an oxygen and a nitrogen heteroatom respectively.

Pyridinyl and pyrimidinyl are examples of 6-membered heteroaryl groups containing one nitrogen and two nitrogen atoms respectively.

Naphthyl is an example of a polycyclic aryl group which has a 10 carbon atom framework formed as two fused 6-membered rings.

As indicated, the aryl group may be substituted at one or more positions, and suitable substituents may be independently selected, at each substituent position, from those substituents which define $R^1$ or $R^2$.

The substituents may be bonded to the aryl group directly or via a group which is independently selected from —O—, —S—, —N— or —$(CR^{10}R^{11})_n$— wherein, n is an integer from 1 to 25, e.g. 1 to 10, such as 1 to 4, and $R^{10}$ and $R^{11}$ are independently at each occurrence selected from alkyl, alkenyl, alkynyl, aryl or heteroaryl, carboxy, alkyloxycarbonyl hydroxyl, amino, morpholino, nitro, alkyloxy, alkylthio, formyl, cyano, carbamoyl, halo (e.g. fluoro, chloro, bromo or iodo), a ketone, —S(O)NR$^7$R$^8$ or —S(O)R$^9$, wherein R$^7$, R$^8$ and R$^9$ are defined as hereinbefore.

Preferred compounds of formula (I) for use as a medicament have the following formula (II):

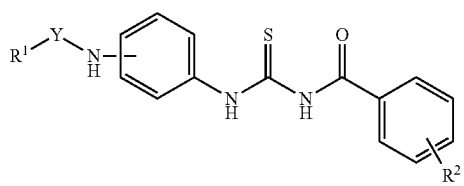

wherein,

R$^1$, R$^2$ and Y are defined as hereinbefore, or a physiologically acceptable salt, solvate, ester or other physiologically functional derivatives thereof.

Preferably, R$^1$YNH— and/or R$^2$— are in the para-position on the respective phenyl rings to which they are bonded.

Preferably Y is the group —C(O)—, thus preferably, the group R$^1$YNH— is R$^1$C(O)NH—.

The present invention also extends to pharmaceutical formulations comprising the compounds of formulae (I) or (II) together with a pharmaceutically acceptable carrier therefor, as explained in further detail below.

The present invention also extends to methods of treatment or prophylaxis comprising administering one or more compounds of formulae (I) or (II) described herein to a patient in need thereof, as described herein below in more detail.

The present invention also extends to novel compounds within the scope of formulae (I) and (II).

Thus, in a further aspect, the present invention provides a compound according to formulae (I) or (II) recited herein, excluding the compounds:

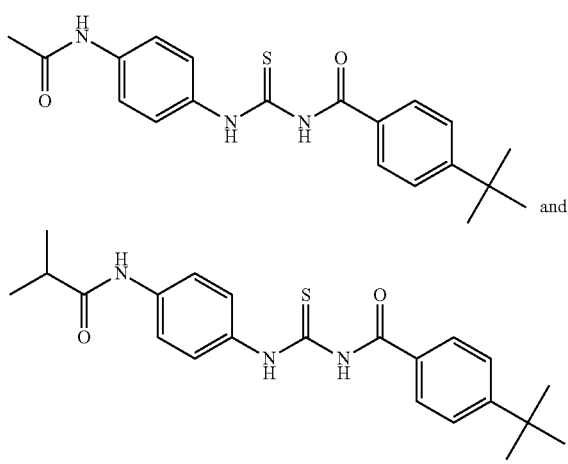

In the compound formulae described herein, an alkyl group may be independently a $C_1$-$C_{22}$ alkyl, preferably a $C_1$-$C_{10}$ alkyl, preferably $C_1$-$C_4$ alkyl, for example, methyl, ethyl, propyl, butyl.

An alkenyl group may be independently a $C_2$-$C_{22}$ alkenyl, preferably a $C_2$-$C_{10}$ alkenyl, preferably $C_2$-$C_4$ alkenyl.

An alkynyl group may be independently a $C_2$-$C_{22}$ alkynyl, preferably a $C_2$-$C_{10}$ alkynyl, preferably $C_2$-$C_4$ alkynyl.

The alkyl, alkenyl or alkynyl groups may be branched or unbranched, substituted or unsubstituted. For example typical branched alkyl groups include iso-propyl, iso-butyl, sec-butyl, tert-butyl, 3-methylbutyl, 3,3-dimethylbutyl and variations, including isomers thereof.

As described herein, the alkyl, alkenyl or alkynyl groups may be substituted, and the substituents may be any chemical moiety such as a hydroxyl, substituted or unsubstituted amine, substituted or unsubstituted amide, halide (such as fluoro, chloro, bromo, iodo), alkoxy, thio, nitro, carboxy, an ester, cyano, or aryl (such as phenyl, naphyl and pyridyl).

The geometry of the double bonds in the compounds described herein, e.g. in the alkenyl groups may be in the cis- or trans-geometry.

Examples of physiologically acceptable salts of the compounds according to the invention include acid addition salts formed with organic carboxylic acids such as acetic, lactic, tartaric, maleic, citric, pyruvic, oxalic, fumaric, oxaloacetic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids.

Physiologically functional derivatives of compounds of the present invention are derivatives, which can be converted in the body into the parent compound. Such physiologically functional derivatives may also be referred to as "pro-drugs" or "bioprecursors". Physiologically functional derivatives of compounds of the present invention include in vivo hydrolysable esters.

It may be convenient or desirable to prepare, purify, and/or handle a corresponding solvate of the compounds described herein, which may be used in the any one of the uses/methods described. The term solvate is used herein to refer to a complex of solute, such as a compound or salt of the compound, and a solvent. If the solvent is water, the solvate may be termed a hydrate, for example a mono-hydrate, di-hydrate, tri-hydrate etc, depending on the number of water molecules present per molecule of substrate.

It will be appreciated that the compounds of the present invention may exist in various stereoisomeric forms and the compounds of the present invention as hereinbefore defined include all stereoisomeric forms and mixtures thereof, including enantiomers and racemic mixtures. The present invention includes within its scope the use of any such stereoisomeric form or mixture of stereoisomers, including the individual enantiomers of the compounds of formulae (I) or (II) as well as wholly or partially racemic mixtures of such enantiomers.

The compounds of the present invention may be prepared using reagents and techniques readily available in the art and as described hereinafter. Novel intermediate compounds in the synthetic route for preparation of the compounds of the present invention may be important molecules for general application for the preparation of the molecules of the present invention. Accordingly, the present invention extends to include those novel intermediate compounds.

As an example, the compounds may be synthesised using methods described in European Patent, publication number EP 0 136 745 B1 and European Patent Application, publication number EP 0 193 249 A2.

Useful synthetic methods for preparing the compounds according to formula (II) include treating various benzoyl chlorides with a metal thiocyanate (e.g. sodium thiocyanate) in a solvent (e.g. actetone) to provide benzoyl isothiocyanates, which are then reacted (preferably in situ) with anilines to provide the desired compounds according to formula (II) as shown in the following scheme:

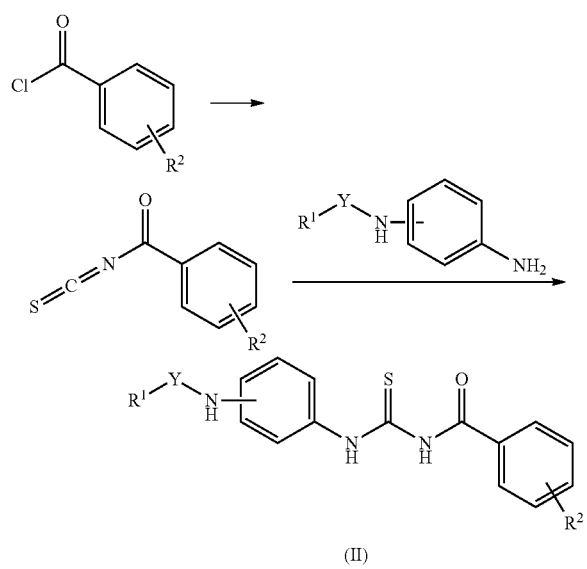

(II)

In the above scheme, the phenyl groups are representative of any aryl group. Further functionalisation may be achieved by acylation or alkylation. Under basic aqueous conditions, the compounds can undergo hydrolysis to provide N-arylthioureas.

As indicated above, the present invention provides a treatment or prophylaxis of a disease, pathology or condition recited herein comprising administering a compound recited herein to a patient in need thereof.

Diseases relevant to the present invention include those involving abnormal cell death associated with abnormalities with the p53 protein, its function and/or the p53 pathway.

In particular, diseases involving abnormal proliferation of cells are treatable with the compounds recited herein. Examples of such diseases include cancers, hyperproliferation disorders (including warts, psoriasis, inflammatory bowel disease), rheumatoid/autoimmune conditions, sickle cell anemia, thalasemias and the like.

Examples of cancers which may be treated by the active compounds include, but are not limited to, a carcinoma, for example a carcinoma of the bladder, breast, colon (e.g. colorectal carcinomas such as colon adenocarcinoma and colon adenoma), kidney, epidermal, liver, lung, for example adenocarcinoma, small cell lung cancer and non-small cell lung carcinomas, oesophagus, gall bladder, ovary, pancreas e.g. exocrine pancreatic carcinoma, stomach, cervix, thyroid, prostate, or skin, for example squamous cell carcinoma; a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma; a hematopoietic tumor of myeloid lineage, for example acute and chronic myelogenous leukemias, myelodysplastic syndrome, or promyelocytic leukemia; thyroid follicular cancer; a tumour of mesenchymal origin, for example fibrosarcoma or habdomyosarcoma; a tumor of the central or peripheral nervous system, for example astrocytoma, neuroblastoma, glioma or schwannoma; melanoma; seminoma; teratocarcinoma; osteosarcoma; xenoderoma pigmentoum; keratoctanthoma; thyroid follicular cancer; or Kaposi's sarcoma.

The present inventors have now observed that compounds of the present invention, such as JH164 identified herein, are particularly effective in inhibiting SirT1 activity. Thus, compounds of the invention, such as JH164, may be of use in treating diseases/conditions associated with SirT1 expression/function.

SirT1 or related proteins have been identified as being a target in a great many diseases/conditions, including cancer, ageing, diabetes, muscle differentiation, heart failure, neurodegeneration, HIV infection and malaria (see for example, Bordone L, Guarente L. Cancer Res. 2006 Apr. 15; 66(8): 4368-77; Heltweg et al *Trends Pharmacol Sci.* 2005 February; 26(2):94-103; Pagans et al; *PLoS Biology* 2005 Vol. 3, No. 2, e41; Deitsch K W, Cell. 2005 Apr. 8; 121(1):1-2; Freitas-Junior L H et al, Cell. 2005 Apr. 8; 121(1):25-36, Nayagam V M, J Biomol Screen. 2006 Nov. 12 and so the compounds of the present invention may find utility in treating/preventing any of the aforementioned diseases/conditions.

Examples of other therapeutic agents that may be administered together (whether concurrently or at different time intervals) with the compounds of the formula (I) include but are not limited to topoisomerase inhibitors, alkylating agents, antimetabolites, DNA binders and microtubule inhibitors (tubulin target agents), such as cisplatin, cyclophosphamide, doxorubicin, irinotecan, fludarabine, 5FU, taxanes, mitomycin C or radiotherapy. For the case of active compounds combined with other therapies the two or more treatments may be given in individually varying dose schedules and via different routes.

The combination of the agents listed above with a compound of the present invention would be at the discretion of the physician who would select dosages using his common general knowledge and dosing regimens known to a skilled practitioner.

Where the compound of the formula (I) is administered in combination therapy with one, two, three, four or more, preferably one or two, preferably one other therapeutic agents, the compounds can be administered simultaneously or sequentially. When administered sequentially, they can be administered at closely spaced intervals (for example over a period of 5-10 minutes) or at longer intervals (for example 1, 2, 3, 4 or more hours apart, or even longer period apart where required), the precise dosage regimen being commensurate with the properties of the therapeutic agent(s).

The compounds of the invention may also be administered in conjunction with non-chemotherapeutic treatments such as radiotherapy, photodynamic therapy, gene therapy; surgery and controlled diets.

The patient is typically an animal, e.g a mammal, especially a human.

For use according to the present invention, the compounds or physiologically acceptable salt, solvate, ester or other physiologically functional derivative thereof described herein may be presented as a pharmaceutical formulation, comprising the compound or physiologically acceptable salt, ester or other physiologically functional derivative thereof, together with one or more pharmaceutically acceptable carriers therefore and optionally other therapeutic and/or prophylactic ingredients. The carrier(s) must be acceptable in the sense of being compatible with the other ingredients of the formulation and not deleterious to the recipient thereof.

Pharmaceutical formulations include those suitable for oral, topical (including dermal, buccal and sublingual), rectal or parenteral (including subcutaneous, intradermal, intramuscular and intravenous), nasal and pulmonary administration e.g., by inhalation. The formulation may, where appropriate, be conveniently presented in discrete dosage units and may be prepared by any of the methods well known in the art of pharmacy. All methods include the step of bringing into association an active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active compound. A tablet may be made by compression or moulding, optionally with one or more accessory ingredients. Compressed tablets may be prepared by compressing in a suitable machine an active compound in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersable granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active compound is formulated in an appropriate release—controlling matrix, or is coated with a suitable release—controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active compound with the softened or melted carrier(s) followed by chilling and shaping in moulds.

Pharmaceutical formulations suitable for parenteral administration include sterile solutions or suspensions of an active compound in aqueous or oleaginous vehicles.

Injectable preparations may be adapted for bolus injection or continuous infusion. Such preparations are conveniently presented in unit dose or multi-dose containers which are sealed after introduction of the formulation until required for use. Alternatively, an active compound may be in powder form which is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient.

As one possibility such formulations are in the form of finely comminuted powders which may conveniently be presented either in a pierceable capsule, suitably of, for example, gelatin, for use in an inhalation device, or alternatively as a self-propelling formulation comprising an active compound, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active compound is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microlitres, upon each operation thereof.

As a further possibility an active compound may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

It should be understood that in addition to the aforementioned carrier ingredients the pharmaceutical formulations described above may include, an appropriate one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

Pharmaceutically acceptable carriers are well known to those skilled in the art and include, but are not limited to, 0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Formulations suitable for topical formulation may be provided for example as gels, creams or ointments. Such preparations may be applied e.g. to a wound or ulcer either directly spread upon the surface of the wound or ulcer or carried on a suitable support such as a bandage, gauze, mesh or the like which may be applied to and over the area to be treated.

Liquid or powder formulations may also be provided which can be sprayed or sprinkled directly onto the site to be treated, e.g. a wound or ulcer. Alternatively, a carrier such as a bandage, gauze, mesh or the like can be sprayed or sprinkle with the formulation and then applied to the site to be treated.

Therapeutic formulations for veterinary use may conveniently be in either powder or liquid concentrate form. In accordance with standard veterinary formulation practice, conventional water soluble excipients, such as lactose or sucrose, may be incorporated in the powders to improve their physical properties. Thus particularly suitable powders of this invention comprise 50 to 100% w/w and preferably 60 to 80% w/w of the active ingredient(s) and 0 to 50% w/w and preferably 20 to 40% w/w of conventional veterinary excipients. These powders may either be added to animal feedstuffs, for example by way of an intermediate premix, or diluted in animal drinking water.

Liquid concentrates of this invention suitably contain the compound or a derivative or salt thereof and may optionally include a veterinarily acceptable water-miscible solvent, for example polyethylene glycol, propylene glycol, glycerol, glycerol formal or such a solvent mixed with up to 30% v/v of ethanol. The liquid concentrates may be administered to the drinking water of animals.

The present invention will now be described with reference to the following non-limiting examples.

BRIEF DESCRIPTION OF THE DRAWINGS

The present invention will now be described with reference to the following drawings in which.

DETAILED DESCRIPTION

Compound Synthesis

Figure 1:
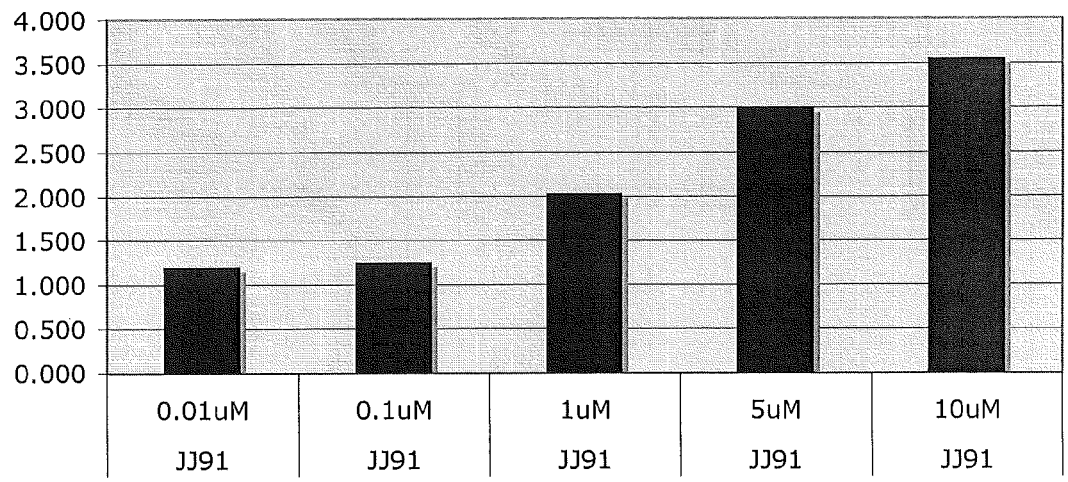
FIG. 1 is a chart showing the amount of fold induction of p53-dependent transcription in T22 RGC-ΔFos-lacZ cells treated with varying amounts of the compound JJ91.

Compounds described herein were provided according to the following methods, with reference to Schemes 1 and 2.

Referring to Scheme 1, the N-benzoylthioureas described in the present invention were synthesised by providing various benzoyl chlorides which were treated with sodium thiocyanate in acetone solvent to provide benzoyl isothiocyanates, which were then reacted in situ with anilines to provide the desired compounds.

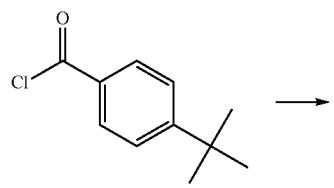

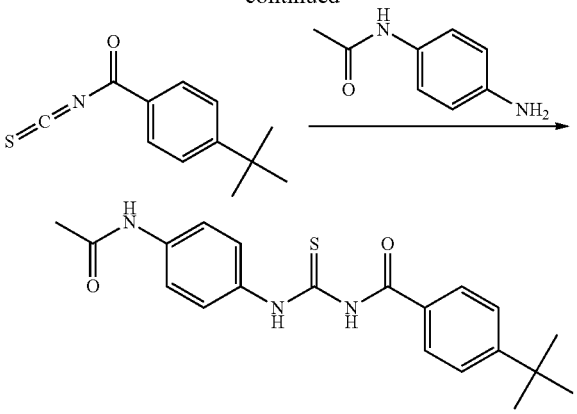

Further functionalisation was achieved by acylation or alkylation.

As an example, the synthesis of a compound (JH129) was achieved as follows:

To a stirred solution of 4-tert-butylbenzoyl chloride (10 mmol, 1.97 g) in acetone (20 mL) under argon atmosphere was added sodium thiocyanate (10 mol, 0.81 g). After 2 h this mixture was added dropwise to a solution of 1,4-phenylenediamine (20 mmol, 2.16 g) in acetone (50 mL) under argon that was cooled to 0° C. After warming to ambient temperature the reaction mixture was stirred for 36 h. The mixture was concentrated in vacuo to a residue that was taken up into dichloromethane, filtered and the filtrate was concentrated and chromatographed on a silica gel column, eluting with ethyl acetate—petroleum ether mixture. Trituration of the resultant solid with diethyl ether provided analytically pure material, 2.45 g (75%). Analysis provided the following data: mpt 189-191° C.; $^1$H-NMR (CDCl$_3$) δ 1.36 (s, 9H), 6.81 (m, 2H), 7.47 (m, 2H), 7.54 (m, 2H), 7.81 (m, 2H), 9.05 (s, 1H), 12.41 (s, 1H); MS (ES+) m/z 350 [M+Na]$^+$; calc'd for C$_{18}$H$_{21}$N$_3$ONaS 350.1300, found 350.1303.

As a further example, the compound JH129 was further functionalised by acylation as follows:

To a stirred solution of JH129 (0.2 mmol, 65 mg) in dichloromethane (1 mL) under argon atmosphere was added a solution of 5-bromopropanoyl chloride (0.2 mmol in 0.2 mL dichloromethane). To the resultant suspension was added triethylamine (0.2 mmol, 27 µL). The reaction mixture was stirred for 90 min before diluting with dichloromethane (5 mL) and washing with 1 M HCl, 2 M NaOH and saturated NaCl solutions. The organic layer was dried (MgSO$_4$) and concentrated to an off-white solid. Recrystallisation from ethyl acetate provided analytically pure material, 64 mg (65%). Analysis provided the following data: mpt 152-153° C.; $^1$H-NMR (CDCl$_3$) δ 1.36 (s, 9H), 1.92 (m, 4H), 2.42 (t, 2H), 3.46 (t, 2H), 7.22 (s, 1H), 7.57 (m, 4H), 7.68 (m, 2H), 7.82 (m, 2H), 9.04 (s, 1H), 12.60 (s, 1H); MS (ES+) m/z 512, 514 [M+Na]$^+$; calc'd for C$_{23}$H$_{28}$$^{79}$BrN$_3$O$_2$NaS 512.0983, found 512.0995.

As a further example, the compound JH164HCl is an example compound wherein the R$^1$ group in formula (I) may be considered to be a linker group to link the active compound to a water soluble group; the synthesis of JH164 and formation of the hydrochloride salt thereof was achieved as follows:

To a solution of JH140 (0.1 mmol, 50 mg) in dichloromethane (10 mL) was added an aqueous solution of dimethylamine (2 mL of 40 wt %). The biphasic mixture was stirred for 20 h. The organic layer was separated, dried (MgSO$_4$) and evaporated to dryness. The residue was dissolved in acetone and this solution was exposed to HCl vapour. The resultant HCl salt was isolated by filtration as a fine white solid, 33 mg (67%). Analysis provided the following data: mpt 205-206° C.; $^1$H-NMR (D$_6$-DMSO) δ 1.32 (s, 9H), 1.64 (brs, 4H), 2.39 (t, 2H), 2.75 (s, 6H), 3.06 (t, 2H), 7.60 (m, 6H), 7.94 (m, 2H), 9.64 (brs, <1H), 10.11 (s, 1H), 11.45 (s, 1H), 12.60 (s, 1H); MS (ES+) m/z 455 [M-Cl]$^+$; calc'd for C$_{25}$H$_{35}$N$_4$O$_2$S 455.2481, found 455.2477; anal. calc'd for C$_{25}$H$_{35}$ClN$_4$O$_2$S: C, 61.14; H, 7.18; N, 11.41%. Found: C, 60.75; H, 7.46; N, 11.30%.

Biological Assesment

In Vitro Experiments:

Materials and Methods:

A 30,000 compound library (DIVERSet™) obtained from Chembridge Chemicals (ChemBridge Corporation 16981 Via Tazon, Suite G San Diego, Calif. 92127) was screened for activators of p53 tumour suppressor function.

The primary and secondary screens were performed using the following cell-based assays.

1. Primary Screen

T22 RGC-ΔFos-lacZ cells expressing beta-galactosidase under the control of a p53-dependent promoter were used and are described by Lu X, Burbidge S A, Griffin S, and Smith H M in Oncogene. 1996 Jul. 18; 13(2):413-8.

- Seed low passage T22 cells at 1×10$^4$ cells per well in a 96-well tissue culture plate with 90 μl selection free DMEM, 10% FCS and 1 mg/ml gentamycin
- The compounds are added 48 hours after cell seeding. DMSO should not exceed 1:100 final concentration in medium. Use an untreated control and a positive control treated with 5 ng/ml actinomycin D. Total volume=100 μl
- Remove medium from 96 well plate after 18 h and add 50 μl 1× lysis buffer (Promega) per well
- Shake for 1 hour at room temperature (can freeze plate at −80° C. until ready to use)
- Add 150 μl CPRG reaction mix per well,
  Preparation of 15 ml CPRG reaction mix:
  15 ml 0.1M phosphate buffer, pH7.5
  300 μl CPRG 4 mg/ml (Boehringer-Mannheim)
  80 μl (0.1 M MgCl$_2$/0.1 M β-mercaptoethanol)
- Incubate 4 hours at 37° C. in a damp chamber. If colour changes from yellow to pink, this indicates p53 activity
- Transfer 100 μl from each well to a new 96 well plate. This prevents cell debris from interfering with absorbance reading. Measure absorbance at 570 nM using plate reader
- Leave lysate overnight at 4° C., then measure the absorbance again 2. Facs Analysis Neuroblastoma cell lines SKNSH-CMVNeo (with functional p53) and SKNSH-DDp53 (inactivated p53) were used and are described by Smart P, Lane E B, Lane D P, Midgley C, Vojtesek B, Lain S. in Oncogene. 1999 Dec. 2; 18(51):7378-86.

Day 1
- Seed 50,000 cells per well of a 6 well plate in DMEM-10% FCS

Day 2
- Add drugs to cells

Day 4
- Add bromodeoxyuridine (BrdU) to 30 μM and incubate cells for 20 minutes.
- Remove media from cells and transfer to a 13 ml Falcon tube. Rinse cells with PBS and transfer this also. Trypsinise cells and transfer to tube then finally rinse with PBS again. Once all transferred to tube, pellet cells at 1500 rpm for 5 minutes.
- Resuspend cells in 1 ml of PBS and add drop wise to 3 ml of ethanol while vortexing. Incubate for a minimum of 1-2 hours at 4° C. (no maximum).

Day 5
- Pellet by centrifugation at 2,500 rpm for 5 minutes then pour off supernatant.
- Prepare 2 ml fresh pepsin solution per tube at 1 mg/ml in 30 mM HCl (pH 1.5) and prewarm to 37° C.
- Add 2 ml prewarmed pepsin solution to each tube and mix for 30 mins at 37° C.
- Pellet by centrifugation at 2500 rpm for 5 minutes then pour off supernatant (pellets will be clear)
- Add 1 ml 2M HCl for 15-20 mins at room temperature (stock bottle is 11.6 M).
- Timing is critical—incubating for long periods results in broad DNA peaks.
- Top up with PBS then pellet as before.
- Wash again with PBS then once in antibody buffer, pelleting cells each time.
- Antibody buffer: PBS, 0.5% BSA, 0.5% Tween-20
- Resuspend pellet into 200 μl of Becton Dickinson anti-BrdU antibody diluted 1:50 in antibody buffer. Incubate for 1 h at room temperature.
- Wash in PBS and pellet cells.
- Resuspend pellet in 200 μl Sigma FITC antibody (#3008) diluted 1:64 in antibody buffer. Incubate for 30 min at room temperature in the dark to prevent the antibody fading.
- Wash in PBS and pellet cells.
- Resuspend final pellet in 500 μl PBS containing 25 μg/ml propidium iodide counter stain. Keep on ice in the dark until analysed on the FACScan.
- Measure DNA content (propidium iodide fluorescence) and DNA synthesis (BrdU incorporation) by FACScan.

3. Western Blotting
- Seed 2×10$^5$ MCF-7 cells per well of a six well plate
- After 24-36 hours incubation add drug to cells and incubate for the time required.
- Pour medium off plates and wash in PBS. Aspirate off the last of the PBS and add 100 μl 1×LDS loading buffer (Invitrogen) directly to the plates. Scrape the surface of the plate into one corner and pipette cells/LDS into a tube
- Heat samples to 90° C. for 5 min then sonicate twice for 15 seconds each. Centrifuge at top speed for 5 min then keep on ice until required.
- Measure protein concentration of all samples (Pierce BCA kit) and equalize their levels. Add 1:10 DTT to each sample.
- Samples are loaded on 4-12% Novex gels, these are run in MOPS buffer×1 and transferred to PVDF membranes according to manufacturers instructions (Invitrogen).
- Membranes are blocked, incubated in primary and then secondary antibodies using standard procedures. Amersham ECL was used for detection.
- Relevant primary antibodies include anti-p53 DO1 mouse monoclonal antibody, anti p53 phosphoserine-15 (Santa Cruz), anti p21 118 mouse monoclonal antibody. Actin detection is used as a loading control.

Results

The results shown in FIG. 1 indicate that JJ91 activates p53's transcription factor function. T22 RGC-ΔFos-lacZ cells were treated with the indicated amounts of JJ91 for 16 hours. Fold induction of p53-dependent transcription was measured.

Figure 2:
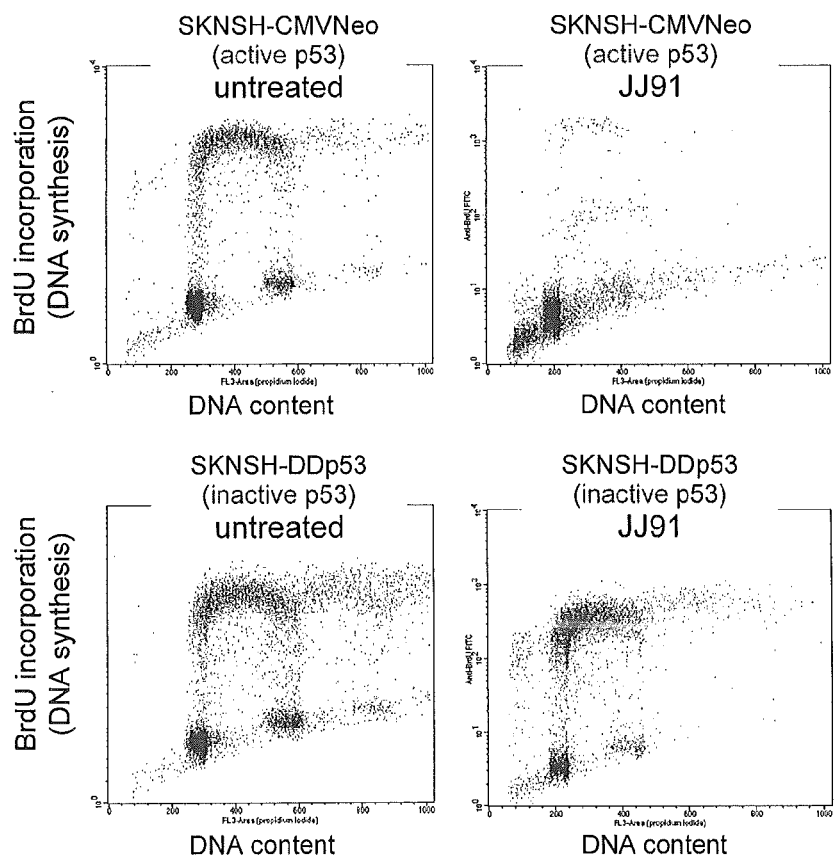
FIG. 2 shows Western Blot images.

The results shown in FIG. 2 indicate that JJ91 selectively kills neuroblastoma cells with active p53. SKNSH-CMVNeo and SKNSH-DDp53 cells were left untreated or treated with 10 μM JJ91 for 48 hours. Cells were analysed by FACS analysis. JJ91 clearly decreases DNA synthesis and cases cell death (increase in the number of sub-G1/G0 cells). These effects are not observed in SKNSH cells with inactive p53.

Figure 3:
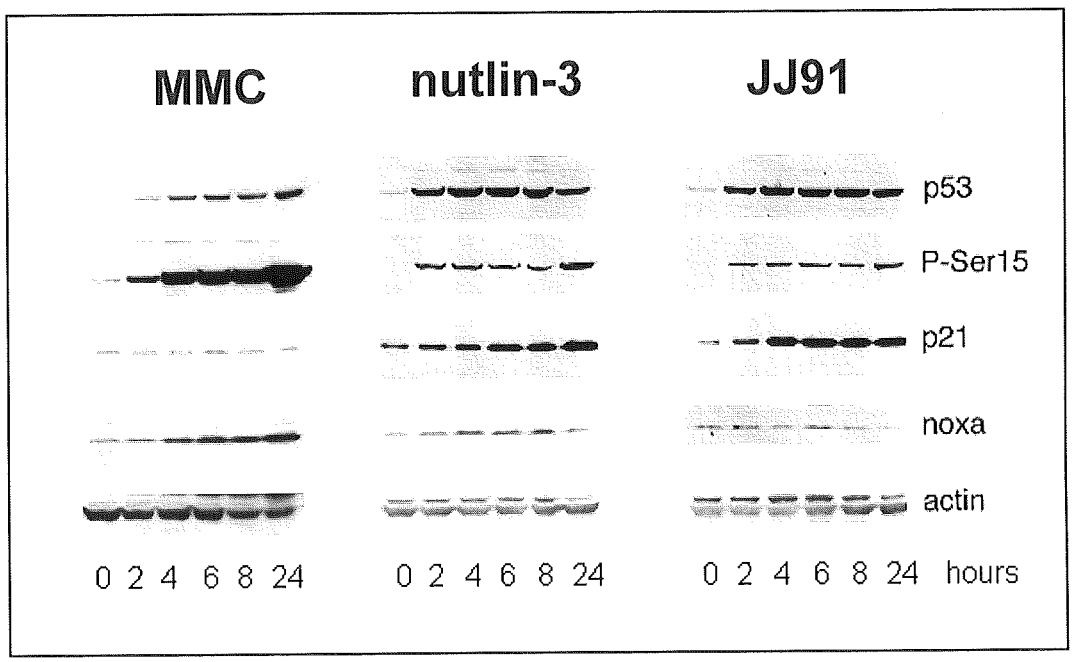
FIG. 3 is FACS analysis graph.

The results shown in FIG. 3 indicate that JJ91 increases p53 levels. MCF-7 cells were treated for the indicated times with the DNA damaging agent mitomycin C (10 μM), the non-genotoxic agent nutlin-3 (6 μM) or JJ91 (10 μM). JJ91 has effects similar to those of nutlin-3. Levels of p53 are rapidly increased. Levels of p53 phosphoserine-15 are not as high as those observed with the genotoxic gent mitomycin C. Levels of the p53 downstream target p21 are increased Actin was analysed as a loading control.

Figures 4A, 4B:
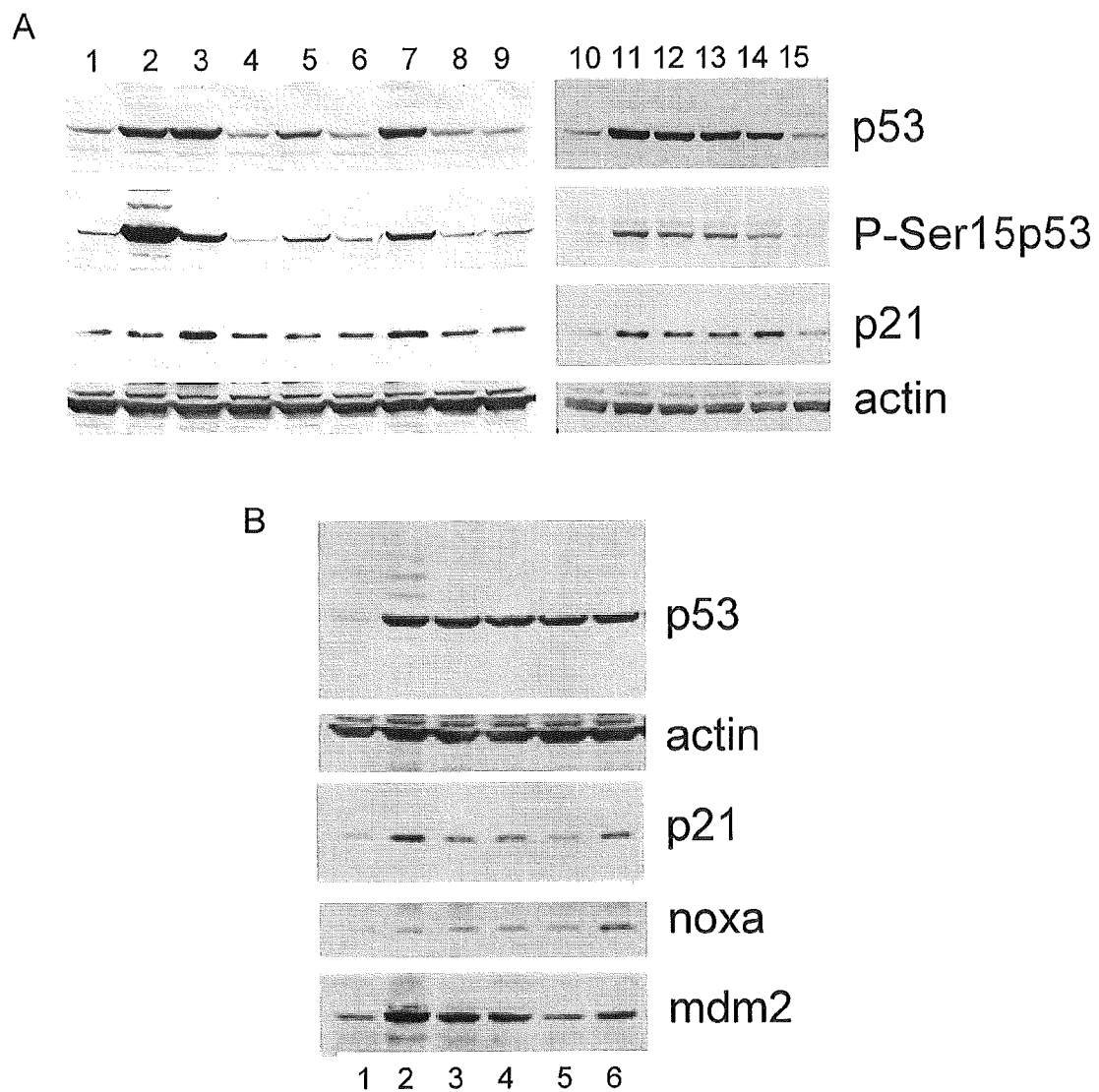
FIGS. 4A and 4B show Western blot images.

The results shown in FIGS. 4A and 4B indicate the effects of JJ91 analogues on p53 levels.

FIG. 4A: MCF-7 cells were treated for 4 hours (lanes 2 through 9) or 6 hours (lanes 11 through 15) with 10 μM mitomycin C (lane 2), JJ91 (lanes 3 and 11), JH118 (lane 4), JH129 (lane 5), JH132 (lane 6), JH140 (lanes 7 and 12), JH141 (lane 8) and 4-aminoacetanilide (lane 9), JH151 (lane 13), JH156 (lane 14) and 5406085 (lane 15). In lanes 2 and 10, cells were left untreated. Cell extracts were analysed by western blotting with antibodies against p53, posphoserine-15 p53, p21 and actin.

FIG. 4B: MCF-7 cells were treated for 4 hours (lanes 2 through 6) 6 μM nutlin-3 (lane 2), 10 μM JJ91 (lane 3), 10 μM 7322366 (lane 4), 40 nM leptomycin B (lane 5) and 20 μM MG132 JH129. Cell extracts were analysed by western blotting with antibodies against p53, actin, p21, noxa and mdm2.

Table 1 shows the structure of active compounds, and the level of activity with respect to p53-dependent transcription in T22 RGC-ΔFos-lacZ cells by the indicated compounds, taking compound JJ91 activity as 100%.

TABLE 1

| ID | Structure | Bioactivity (relative to JJ91) |
|---|---|---|
| JJ91 | 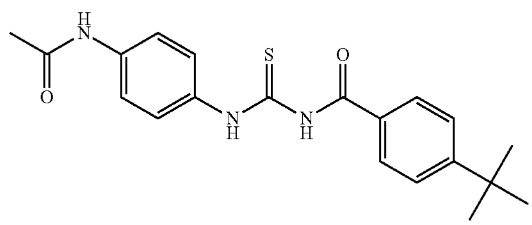 [SMILES: CC(=O)Nc1ccc(NC(=S)NC(=O)c2ccc(C(C)(C)C)cc2)cc1] | Active (100%) |
| 7322366 'JH155' | 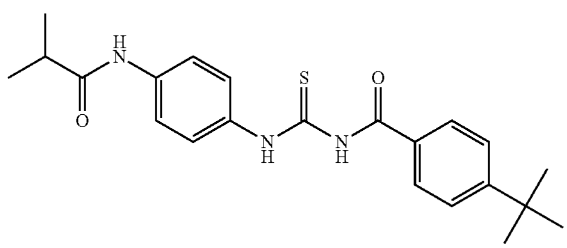 [SMILES: CC(C)C(=O)Nc1ccc(NC(=S)NC(=O)c2ccc(C(C)(C)C)cc2)cc1] | Active (81.2%) |
| JH129 | 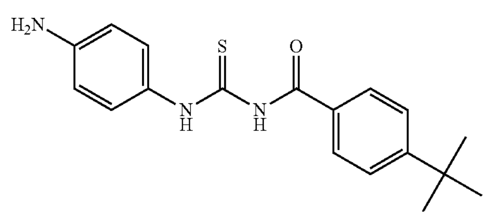 [SMILES: CC(C)(C)c1ccc(C(=O)NC(=S)Nc2ccc(N)cc2)cc1] | Active (<) |
| JH140 | 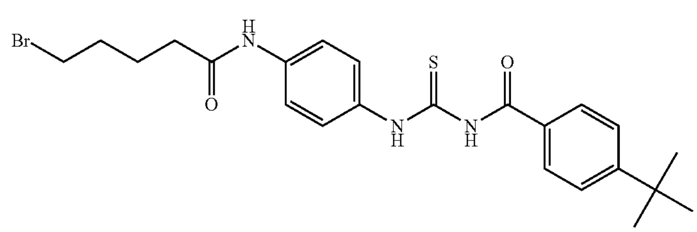 [SMILES: CC(C)(C)c1ccc(C(=O)NC(=S)Nc2ccc(NC(=O)CCCCBr)cc2)cc1] | Active (87.5%) |

TABLE 1-continued

| ID | Structure | Bioactivity (relative to JJ91) |
|---|---|---|
| JH151 | 4-tert-butyl-benzoyl-thiourea-phenyl-NH-benzoyl structure | Active (106.1%) |
| JH156 | 4-tert-butyl-benzoyl-thiourea-phenyl-NH-C(O)-(CH2)3-N-morpholine structure | Active (75.4%) |
| JH156HCl | 4-tert-butyl-benzoyl-thiourea-phenyl-NH-C(O)-(CH2)3-N(H)+-morpholine Cl− structure | Active (59.6%) |
| JH164HCl | 4-tert-butyl-benzoyl-thiourea-phenyl-NH-C(O)-(CH2)3-N(H)+(CH3)2 Cl− structure | Active (63.8%) |

Figure 5:
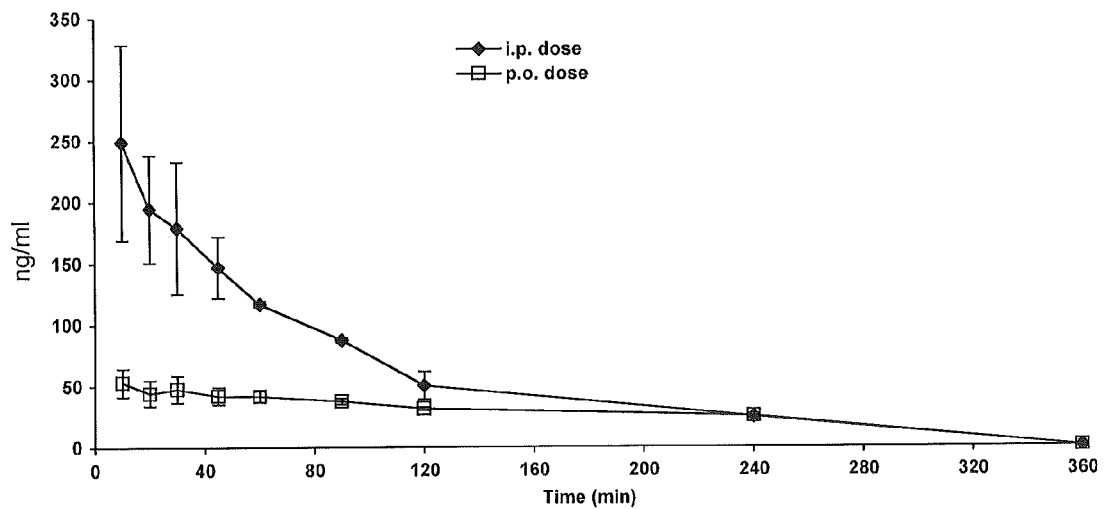
FIG. 5 is a graph showing the results of compound administration to mice.

In vitro and In vivo Experiments:

Referring to FIG. 5, JJ91 was administered to mice at a dose of 5 mg/kg. ♦ and □ correspond to i.p. and p.o. routes of administration respectively (inset shows a logarithmic plot of the data). Blood levels were determined at the times shown by LC-MS/MS above and the values shown are the means±SD for three determinations. The results indicate that intraperitoneal injection of the compounds shows that they reach micromolar concentrations in blood, do not cause significant weight or behavioural changes and have a half-life of approximately 1.3 hours.

Figure 6:
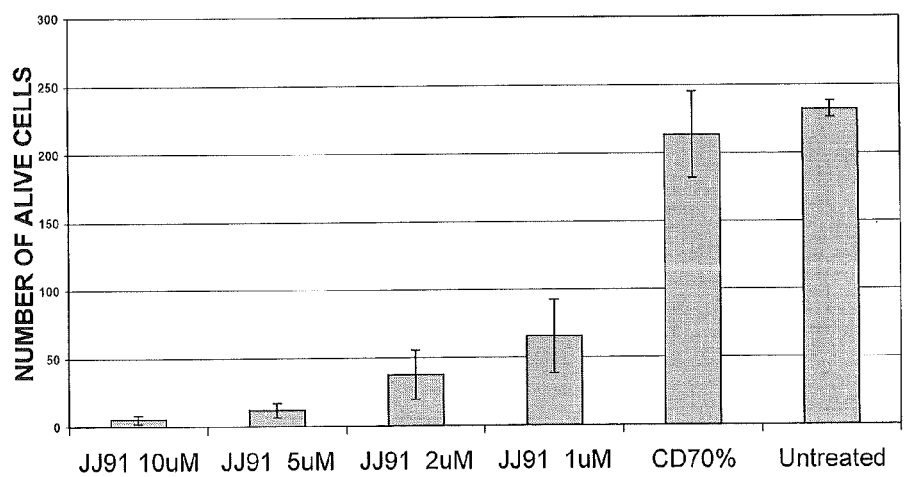
FIG. 6 is a chart showing the effects of varying concentrations of JJ91 on the survival of BL2 Burkitt lymphoma cells.

Referring to FIG. 6, BL2 Burkitt lymphoma cells were treated with the indicated concentrations of JJ91, ranging from 1 μM to 10 μM (dissolved in 70% cyclodextrin), for 2 hours. At this time, the number of live cells were counted. After this short exposure, cells were washed to remove the compound. This treatment was repeated daily for six days. Experiments were performed in triplicate and standard deviations indicated. BL2 cell survival was largely reduced after these six short exposures to the compounds as shown in FIG. 6.

Figure 7:
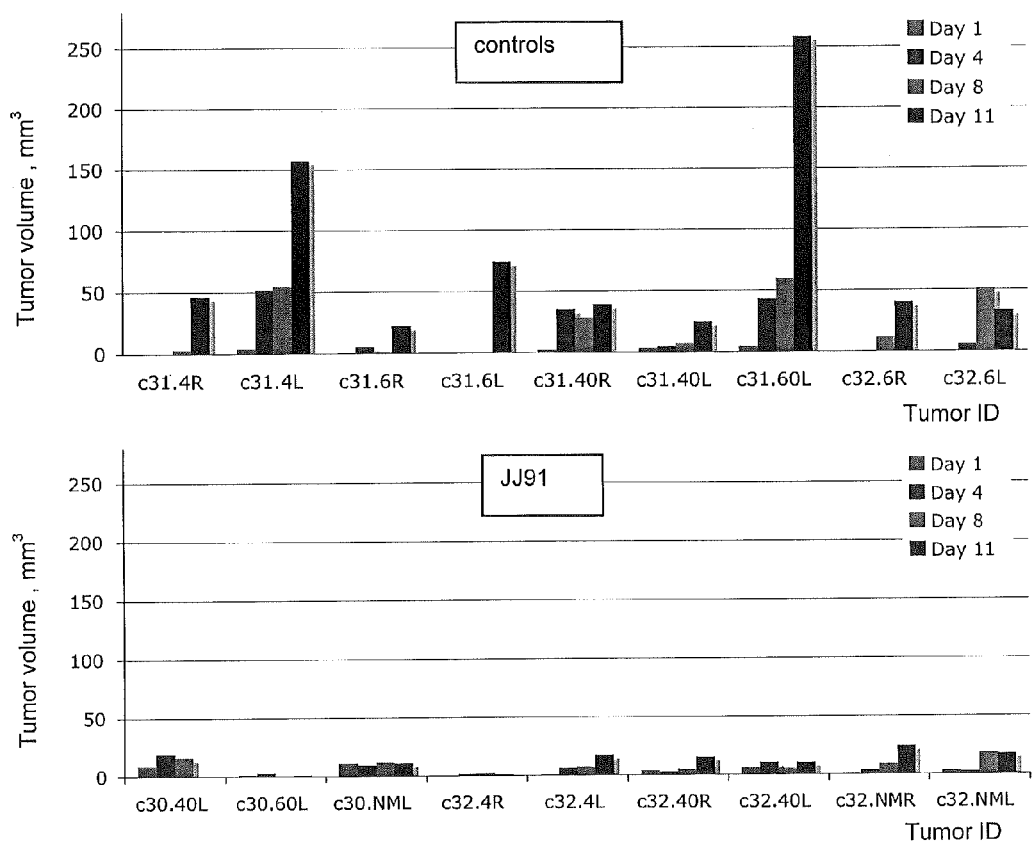
FIG. 7 is a chart showing the effects of JJ91 on BL2 Burkitt lymphoma xenograft tumours in SCID mice.

Referring to FIG. 7, BL2 Burkitt lymphoma xenograft tumours in SCID mice were established for 7 days until tumours were palpable. At this point, vehicle (70% cyclodextrin) (top panel) or JJ91 (92 mg/kg) (bottom panel) was administered daily by intraperitoneal injection. Tumour sizes were measured on the day of injection (day__1) and on days 4, 8 and post-injection. As shown, JJ91 reduces growth of BL2 xenograft tumours in SCID mice.

SirT1 activity was evaluated using the Fluor de Lys SirT1 Fluorescent Activity Assay from Biomol (catalog no. AK-555) as specified by the manufacturer. Reactions contained 1 millimolar NAD+, 7 micromolar Fluor de Lys Substrate and increasing amounts of JH164. Deacetylation and developer reactions were carried out for 1 hour at 37° C. 1050 for JH164 is 23.5 micromolar.

The above embodiments are representative of the present invention and are not to be construed as limiting the scope of the invention as defined in the claims.

The invention claimed is:

1. A method of activating p53 response, said method comprising administering to a subject in need thereof a therapeutically useful amount of a compound according to formula (I):

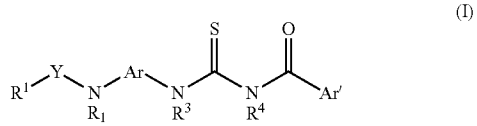

wherein, $R^1$ is independently, in each instance, selected from the group cons sting of H; branched or unbranched mono-, di-, or tri-substituted or unsubstituted alkyi, alkenyl or alkynyl; aryl; and Z-alkyl, Z-alkenyl, Z-alkynyl or Z-aryl, wherein Z is O, NH, N, or S, Y is absent or —C(O)—, —C(S)— or —SO$_2$, Ar is aryl Ar' is a phenyl substituted at one or more available position by a $C_2$-$C_{10}$ branched or unbranched, substituted or unsubstituted alkyl, and $R^3$ and $R^4$ are either:

each independently selected from the group consisting of: H; branched or unbranched mono-, di- or tri-substituted or unsubstituted alkyl; and Z-alkyl, wherein Z is O, NH, N or S, or, $R^3$ and $R^4$ are:

bound together to form a branched or unbranched, substituted or unsubstituted, alkylene or Z-alkene, wherein Z is O, NH, N or S, or a physiologically acceptable salt, solvate or ester thereof, wherein said method is for the treatment of a cancer selected from the group consisting of Burkitt's lymphoma, chronic mvelogenous leukemia (CML), colon cancer, epithelial cancer, gastric cancer and neurobiastoma.

2. The method of claim 1, wherein $R^3$ and $R^4$ are hydrogen or a $C_{1-4}$ alkyl.

3. The method of claim 1, wherein $R^3$ and $R^4$ are hydrogen.

4. The method of claim 1, wherein Y is —C(O)—, —C(S)— or —SO$_2$—.

5. The method of claim 1, wherein Y is —C(O)—.

6. The method of claim 1, wherein Ar' is a phenyl substituted at one or more available position by a $C_2$-$C_{10}$ branched or unbranched, substituted or unsubstituted alkyl.

7. The method of claim 1, wherein Ar' is a phenyl substituted by a branched alkyl group.

8. The method of claim 7, where the branched alkyl group is isopropyl or tert butyl.

9. The method of claim 7, wherein the branched alkyl group is positioned in the para position of the phenyl ring to which it is bonded.

10. The method of claim 1, wherein the portion $R^1$—Y—N($R^1$)— of formula (I) is $R^1$—Y—N(H)—.

11. The method of claim 6, wherein the compound is of formula (II):

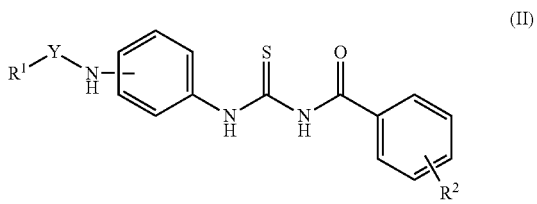

wherein $R^2$ is said $C^2$-$C_{10}$ branched or unbranched, substituted or unsubstituted alkyl.

12. The method of claim 11, wherein $R^1$—Y—NH— is $R^1C(O)NH$—.

13. The method of claim 11, wherein the groups $R^1$—NH— and/or $R^2$— are in the para-position on the respective phenyl rings to which they are bonded.

14. The method of claim 10, wherein $R^1$ in $R^1$—Y—N(H)— is H, or a substituted or unsubstituted alkyl or aryl group.

15. The method of claim 14, wherein the alkyl group is a $C_3$-$C_6$ straight chain alkyl.

16. The method of claim 14, wherein $R^1$ is an alkyl or aryl group substituted one or more times with a group independently selected, at each occurrence, from the group consisting of alkyl, alkenyl, alkynyl, aryl or heteroaryl, carboxy, alkyloxycarbonyl hydroxyl, amino, nitro, alkyloxy, alkylthio, formyl, cyano, carbamoyl, halo, a ketone, —S(O)NR$^7$R$^8$ or —S(O)R$^9$, wherein $R^7$, $R^8$ and $R^9$ are each independently selected from the group consisting of alkyl, alkenyl, alkynyl, aryl and heteroaryl.

17. The method of claim 14, wherein the alkyl group is substituted at the free terminal end with a substituent selected from the group consisting of phenyl, hydroxyl, amino, nitro, alkyloxy, alkylthio, formyl, cyano, carbamoyl, halo, a ketone, —S(O)NR$^7$R$^8$ and —S(O)R$^9$, wherein $R^7$, $R^8$ and $R^9$ are each independently selected from the group consisting of alkyl, alkenyl, alkynyl, aryl and heteroaryl.

18. The method of claim 10, wherein $R^1$ in $R^1$—Y—N(H)— is amino.

19. The method of claim 18, wherein amino is morpholino.

20. The method of claim 18, wherein the amine substituent is protonated.

21. A method of inhibiting sirtuin 1(SirT1) expression and/or function, said method comprising administering to a subject in need thereof a therapeutically useful amount of a compound of formula (I):

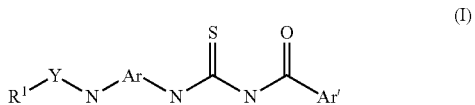

wherein, $R^1$ is independently, in each instance, selected from the group consisting of H; branched or unbranched mono-, di-, or tri-substituted or unsubstituted alkyl, alkenyl or alkynyl; aryl; and Z-alkyl, Z-alkenyl, Z-alkynyl or Z-aryl, wherein Z is O, NH, N, or S, Y is absent or —C(O)—, —C(S)— or —SO$_2$—, Ar is aryl Ar' is a phenyl substituted at one or more available position by a $C_2$-$C_{10}$ branched or unbranched, substituted or unsubstituted alkyl, and $R^3$ and $R^4$ are, either:

each independently selected from the group consisting of: H; branched or unbranched mono-, di- or tri-substituted or unsubstituted alkyl; and Z-alkyl, wherein Z is O, NH, N or S, or, $R^3$ and $R^4$ are:

bound together to form a branched or unbranched, substituted or unsubstituted alkylene or Z-alkene, wherein Z is O, NH, N or S, or a physiologically acceptable salt, solvate or ester thereof, wherein said method is for the treatment of a cancer selected from the group consisting of Burkitt's lymphoma, chronic myelogenous leukemia (CML), colon cancer, epithelial cancer, gastric cancer and neuroblastoma.

22. A method of treatment for a cancer selected from the group consisting of Burkitt's lymphoma, chronic myelogenous leukemia (CML), colon cancer, epithelial cancer, gastric cancer and neuroblastoma, said method comprising administering to a subject in need thereof a therapeutically useful amount of a compound according to formula (I):

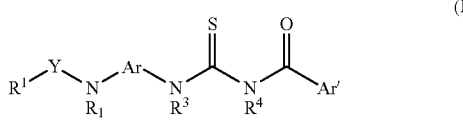

(I)

wherein, $R^1$ is independently, in each instance, selected from the group consisting of H; branched or unbranched mono-, di-, or tri-substituted or unsubstituted alkyl, alkenyl or alkynyl; aryl; and Z-alkyl, Z-alkenyl, Z-alkynyl or Z-aryl, wherein Z is O, NH, N, or S, Y is absent or —C(O)—, —C(S)— or —SO$_2$—, Ar is aryl Ar' is a phenyl substituted at one or more available position by a $C_2$-$C_{10}$ branched or unbranched, substituted or unsubstituted alkyl, and $R^3$ and $R^4$ are, either;

each independently selected from the group consisting of H; branched or unbranched mono-, di-or tri-substituted or unsubstituted alkyl; and Z-alkyl, wherein Z is O, NH, N or S, or, $R^3$ and $R^4$ are:

bound together to form a branched or unbranched, substituted or unsubstituted alkylene or Z-alkene, wherein Z is O, NH, N or S, or a physiologically acceptable salt, solvate or ester thereof.

23. The method of claim 1, wherein said compound is administered in a pharmaceutical composition comprising said compound together with a pharmaceutically acceptable carrier thereof.

24. The method of claim 21, wherein said compound is administered in a pharmaceutical composition comprising said compound together with a pharmaceutically acceptable carrier thereof.

25. The method of claim 22, wherein said compound is administered in a pharmaceutical composition comprising said compound together with a pharmaceutically acceptable carrier thereof.

26. The method of claim 1, wherein the cancer is Burkitt's lymphoma or neuroblastoma.

27. The method of claim 21, wherein the cancer is Burkitt's lymphoma or neurobiastema.

28. The method of claim 22, wherein the cancer is Burkitt's lymphoma or neuroblastoma.

* * * * *

UNITED STATES PATENT AND TRADEMARK OFFICE
CERTIFICATE OF CORRECTION

| | | |
|---|---|---|
| PATENT NO. | : 9,120,765 B2 | |
| APPLICATION NO. | : 13/886898 | |
| DATED | : September 1, 2015 | |
| INVENTOR(S) | : Lain et al. | |

It is certified that error appears in the above-identified patent and that said Letters Patent is hereby corrected as shown below:

On Title Page:
Item 54, Title: Please correct "P53 ACTIVATING COMPOUNDS"
        to read -- P53 ACTIVATING COMPOUNDS AND METHODS OF USING THE SAME --

Item (74), Attorney, Agent, or Firm: Please correct "MyersBigel" to read -- Myers Bigel --

In the Specification:
Column 1, Line 1: Please correct "P53 ACTIVATING COMPOUNDS"
        to read -- P53 ACTIVATING COMPOUNDS AND METHODS OF USING THE SAME --

Column 11, Line 44: Please correct "SCID mice; and" to read -- SCID mice. --

Column 18, Line 59: Please correct "8 and post-injection." to read -- 8 and 11 post-injection. --

Column 18, Line 66: Please correct "1050" to read -- IC50 --

In the Claims:
Column 19, Claim 1, Line 20: Please correct "cons sting of H;" to read -- consisting of: H; --
    Line 21: Please correct "alkyi," to read -- alkyl, --
    Line 44: Please correct "mvelogenous" to read -- myelogenous --
    Line 45 and 46: Please correct "neurobiastoma." to read -- neuroblastoma. --

Column 20, Claim 11, Line 14: Please correct "wherein $R^2$ is said $C^2$-$C_{10}$"
        to read -- wherein $R^2$ is a $C_2$-$C_{10}$ --

Column 20, Claim 13, Line 19: Please correct "$R^1$—NH—and/or" to read -- $R^1$-Y-NH- and/or --

Signed and Sealed this
Fifth Day of July, 2016

Michelle K. Lee
*Director of the United States Patent and Trademark Office*

CERTIFICATE OF CORRECTION (continued)
U.S. Pat. No. 9,120,765 B2

Column 20, Claim 21, Line 63: Please correct "of H;" to read -- of: H; --

Column 21, Claim 22, Line 37: Please correct "of H;" to read -- of: H; --

Column 22, Claim 22, Line 9: Please correct "consisting of" to read -- consisting of: --

Column 22, Claim 27, Line 35: Please correct "neurobiastema." to read -- neuroblastoma. --